United States Patent
Dong et al.

(10) Patent No.: US 8,858,926 B2
(45) Date of Patent: Oct. 14, 2014

(54) ANTIBACTERIAL POLYMER EMULSION AND COATING COMPOSITION

(75) Inventors: Xiangting Dong, Shanghai (CN); Shuang Liang, Shanghai (CN); Tao Wang, Shanghai (CN); Qingwei Zhang, Shanghai (CN)

(73) Assignee: Rohm and Haas Company, Philadelphia, PA (US)

( * ) Notice: Subject to any disclaimer, the term of this patent is extended or adjusted under 35 U.S.C. 154(b) by 331 days.

(21) Appl. No.: 13/076,543

(22) Filed: Mar. 31, 2011

(65) Prior Publication Data

US 2011/0243882 A1    Oct. 6, 2011

(30) Foreign Application Priority Data

Mar. 31, 2010  (CN) .......................... 2010 1 0144595

(51) Int. Cl.
| | | |
|---|---|---|
| A01N 55/02 | (2006.01) | |
| A01P 1/00 | (2006.01) | |
| A61L 2/16 | (2006.01) | |
| C11D 3/02 | (2006.01) | |
| C11D 3/37 | (2006.01) | |
| A01N 59/16 | (2006.01) | |
| C09D 5/14 | (2006.01) | |
| A01N 59/20 | (2006.01) | |
| C09D 7/12 | (2006.01) | |
| C09D 5/02 | (2006.01) | |

(52) U.S. Cl.
CPC *A01N 59/16* (2013.01); *C09D 5/14* (2013.01); *A01N 59/20* (2013.01); *C09D 7/12* (2013.01); *C09D 5/024* (2013.01)
USPC .............. 424/78.31; 422/8; 422/28; 510/199; 510/382; 510/475; 510/500; 510/508

(58) Field of Classification Search
USPC .............. 424/78.31; 422/8, 28; 510/199, 382, 510/475, 500, 508
See application file for complete search history.

(56) References Cited

U.S. PATENT DOCUMENTS

| | | | |
|---|---|---|---|
| 5,698,229 A | 12/1997 | Ohsumi | |
| 5,945,032 A | 8/1999 | Breitenbach et al. | |
| 6,444,726 B1 | 9/2002 | Brunt | |
| 7,390,774 B2 | 6/2008 | Ghosh | |
| 7,540,907 B1 * | 6/2009 | Coello et al. ............... | 106/31.01 |
| 2001/0055608 A1 * | 12/2001 | Hymes et al. ................. | 424/443 |
| 2008/0233204 A1 | 9/2008 | Horley | |
| 2009/0297818 A1 * | 12/2009 | Williams et al. ........... | 428/292.4 |

FOREIGN PATENT DOCUMENTS

| | | |
|---|---|---|
| EP | 1584235 A2 | 10/2005 |
| EP | 1941797 A1 | 7/2008 |
| WO | 2012059944 A2 | 5/2012 |

OTHER PUBLICATIONS

European Search Report issued in EP 2371221 dated Jul. 1, 3013.

* cited by examiner

*Primary Examiner* — Ernst V Arnold
*Assistant Examiner* — Hong Yu
(74) *Attorney, Agent, or Firm* — Karl E. Stauss; Cantor Colburn LLP

(57) ABSTRACT

An aqueous antibacterial polymer emulsion and coating compositions are provided. The aqueous antibacterial polymer emulsion comprising a polymer A, an oxidant and a metal complexed with a copolymer B comprising heterocyclic containing monomers; wherein the metal is selected from copper, silver, gold, tin, zinc and combinations thereof; and wherein the emulsion is heat stable. The coating compositions made therefrom provide persistent, broad spectrum antibacterial activity without discoloration problem upon exposure to heat and/or sun light.

11 Claims, No Drawings

ANTIBACTERIAL POLYMER EMULSION AND COATING COMPOSITION

BACKGROUND

This patent application claims the benefit of the earlier filed Chinese Patent Application serial number 201010144595.X filed on Mar. 31, 2010.

This invention relates generally to an antibacterial polymer emulsion and coating compositions made therefrom with improved color stability property upon exposure to heat and/or light.

Inorganic microbiocides on which metal ions are supported frequently exhibit instabilities which cause them to discolor upon exposure to heat or sun light. Hence, these inorganic microbiocides frequently cause aqueous binder emulsions and coating compositions into which they are incorporated to undergo conspicuous changes in coloration. Accordingly, the use of these microbiocides is effectively limited to systems for which such conspicuous changes in coloration can be tolerated.

U.S. Pat. No. 7,390,774 discloses a light stable antimicrobial composition comprising a metal complexed with a polymer containing 1-vinylimidazole as monomer, wherein the metal is selected from copper, silver, gold, tin, zinc and combinations thereof. The antimicrobial composition exhibits better light stable property than the conventional inorganic microbiocides consisting of metal ions supported by materials including active carbon, apatite, zeolite, and various phosphates. However, a higher level of color stability is still desired. Moreover, the antimicrobial composition comprising a metal complexed with a polymer needs some kind of organic solvent and ammonia to help incorporation, which increases the total volatile organic compound (VOC) content of the coating composition and causes bad odor. Low VOC and ammonia free are also desired.

The problem addressed by this invention is to find an improved aqueous antibacterial polymer emulsion which shows lower discoloration of the corresponding formulations upon exposure to heat and/or sun light as compared to the antimicrobial composition of the U.S. Pat. No. 7,390,774. Moreover, this invention also provides an antibacterial polymer emulsion comprising a metal complexed with a polymer that is stripped by steam to remove the VOC and ammonia for low VOC and low odor request.

STATEMENT OF INVENTION

The present invention provides an aqueous antibacterial polymer emulsion comprising, based on the dry weight of the emulsion, from 90 to 99.9 wt % a polymer A, from 0.004 to 1 wt % an oxidant and from 0.002 to 1 wt % a metal complexed with a copolymer B that comprises from 5 to 95 wt % a heterocyclic containing monomer residue; wherein the metal is selected from copper, silver, gold, tin, zinc and combinations thereof; and wherein the emulsion is heat stable.

DETAILED DESCRIPTION

The aqueous antibacterial polymer emulsion of the present invention comprises from 90 to 99.99%, preferably from 95 to 99.9%, more preferably from 99 to 99.9%, a polymer A, in percentage by weight based on the dry weight of the emulsion. Suitable polymer A is selected from emulsion polymers functioned as binders used in coating compositions in the art, including pure acrylic, styrene acrylic and vinyl acetate acrylic emulsion polymers. Examples of the polymer include commercially available polymer emulsions ROVACE™ SF-091, PRIMAL™ AS-2010 and PRIMAL™ E-3131NG from Rohm and Haas Company, a wholly owned subsidiary of The Dow Chemical Company.

The glass transition temperature (Tg) of the polymer A ranges from −35° C. to 60° C., preferably from −15° C. to 40° C., and more preferably from −10° C. to 30° C. Tgs used herein are those calculated by using the Fox equation (T. G. Fox, Bull. Am. Physics Soc., Volume 1, Issue No. 3, page 123, 1956). Tgs of homopolymers may be found, for example, in "Polymer Handbook", edited by J. Brandrup and E. H. Immergut, Interscience Publishers.

The polymerization techniques used to prepare the aqueous emulsion polymers are well known in the art. See (R. Arshady, Colloid and Polymer Science, Vol. 270, 717-732, 1992, or Piirma $I^{ED}$, Emulsion polymerization, Academic Press, New York. 1982).

The average particle diameter of the emulsion polymer particles ranges from 50 to 350 nanometers, preferably from 100 to 300 nanometers, as measured by a BI-90 Particle Sizer. Without being bound by a particular theory, it is believed that lower particle sizes lead to greater emulsion polymer shear instability and that larger particle sizes lead to lower binding capacity and therefore lower scrub resistance.

The aqueous antibacterial polymer emulsion of the present invention comprises, by weight percentage based on the dry weight of the emulsion, from 0.002 to 1%, preferably from 0.003 to 1%, more preferably from 0.02 to 0.5%, a metal complexed with a copolymer B, wherein the metal is selected from copper, silver, gold, tin, zinc and combinations thereof, alternatively the metal is selected from copper, silver, gold and combinations thereof, alternatively the metal is selected from copper, silver and combinations thereof, alternatively the metal is silver.

As used herein and in the appended claims, the term "metal complexed with polymer" herein refers to a metal which is complexed with a copolymer via coordination bond, ion bond or other weak interactions. The content of a "metal complexed with polymer" in a composition of the present invention refers to the content of the metal. The term "silver" herein refers to silver metal that is incorporated into an antibacterial emulsion or composition of the present invention. While not wanting to be bound as to the oxidation state of the silver ($Ag^0$, $Ag^{1+}$), that is incorporated into the antibacterial emulsion or composition, silver may be added to the antibacterial emulsion or composition by washing the copolymer in a silver solution such as silver nitrate in deionized water ("DI"). Aside from DI, other liquid mediums can also be used such as water, aqueous buffered solutions and organic solutions such as polyethers or alcohols. Other sources of silver include but are not limited to silver acetate, silver citrate, silver iodide, silver lactate, silver picrate and silver sulfate. The concentration of silver in these solutions can vary from the concentration required to add a known quantity of silver to the antibacterial emulsion or composition to a saturated silver solution.

In another embodiment of the present invention, the antibacterial polymer emulsion contains 20 to 10,000 ppm metal; alternatively 20 to 4,000 ppm metal; alternatively 20 to 1,500 ppm metal; alternatively 30 to 75 ppm metal; alternatively at least 50 ppm metal.

In another embodiment of the present invention, the antibacterial polymer emulsion contains silver. In one aspect of this embodiment, the antibacterial polymer emulsion contains 20 to 10,000 ppm silver; alternatively 20 to 4,000 ppm silver; alternatively 20 to 1,500 ppm silver; alternatively 30 to 75 ppm silver; alternatively at least 50 ppm silver.

The copolymer B comprises, as copolymerized units, by weight percentage based on the dry weight of the copolymer B, from 5 to 95%, preferably from 10 to 90%, more preferably from 20 to 80%, a heterocyclic containing monomer. In one embodiment, the copolymer B comprises monomer residues selected from residue A, residue B, residue C and mixtures thereof, with the proviso that the polymer contains no more than 99.5 wt % of monomer residues of residue B, alternatively no more than 99 wt % of monomer residues of residue B, alternatively no more than 98 wt % monomer residues of residue B, alternatively no more than 95 wt % of monomer residues of residue B, alternatively no more than 90 wt % of monomer residues of residue B;

wherein residue A is $$-(CH(R_1)-C(R_2)(R_3))-$$

wherein residue B is $$-(CH(R_1)-C(R_2)(X))-$$

and wherein residue C is

[structure of residue C with $R_8$, $R_9$, $(CH_2)_c$, two C=O groups, N-$R_{10}$-X]

wherein

X is selected from an unsaturated or aromatic heterocycle having at least one hetero atom selected from N, O and S; alternatively X is selected from an unsaturated or aromatic heterocycle having at least one hetero N atom;

c is 0 or 1; alternatively c is 0;

$R_1$ is selected from H, $CH_3$ and $-CO_2R_4$; where $R_4$ is selected from H, $CH_3$, $C_2H_5$, a $C_3$-$C_{24}$ alkyl;

$R_2$ is selected from H, $CH_3$, $C_2H_5$, phenyl, $-CH_2CO_2R_5$ and $-CO_2R_5$; where $R_5$ is selected from (I)-(V), $$H; \quad (I)$$

$$H_2C\overset{O}{\triangle}; \quad (II)$$

$$-(CH_2CH(R_{11})O)_nH; \quad (III)$$

$$-(CH_2CH(R_{11})O)_nCOCH_2COCH_3; \quad \text{and} \quad (IV)$$

$$\begin{array}{c} OH \\ | \\ HC-CH_2- \\ / \\ CH_2 \\ \backslash \\ Y \end{array} \quad (V)$$

where $R_{11}$ is selected from H, methyl and phenyl; n is an integer from 1 to 20; Y is selected from OH, $SO_3Z$ and X; where Z is selected from H, sodium, potassium and $NH_4^+$; with the proviso that when the polymer contains 0 wt % of monomer residues of residue B and 0 wt % of monomer residues of residue C, $R_2$ is $-CH_2CO_2R_5$ or $-CO_2R_5$, $R_5$ is (V) and Y is X;

$R_3$ is selected from H, methyl, phenyl, sulfonated phenyl, phenol, acetate, hydroxy, a fragment O—$R_1$, where $R_1$ is as defined previously, $-CO_2R_{12}$ and $-CONR_6R_7$; where $R_6$ and $R_7$ are independently selected from H, methyl, ethyl, $C(CH_3)_2CH_2SO_3Z$, where Z is as defined previously, $C_3$-$C_8$ alkyl and a combined ring structure and $R_{12}$ is selected from H, $CH_3$, $C_2H_5$ and $C_3$-$C_{24}$ alkyl;

$R_8$ and $R_9$ are independently selected from hydrogen, methyl, ethyl and $C_3$-$C_4$ branched or straight chain alkyl; alternatively $R_8$ and $R_9$ are both hydrogen;

$R_{10}$ is selected from $C_1$-$C_8$ alkyl, $C_2$-$C_8$ alkenyl, $C_6$-$C_{10}$ unsaturated acyclic, $C_6$-$C_{10}$ cyclic, $C_6$-$C_{10}$ aromatic, $C_2$-$C_4$ alkylene oxide and poly($C_2$-$C_4$ alkylene)$_b$ oxides; where b is an integer from 2 to 20; alternatively $R_{10}$ is selected from $C_2$-$C_8$ branched and straight chain alkyl groups.

Unsaturated or aromatic heterocycles suitable for use with the present invention include, for example, 5 to 7-membered heterocycles having some degree of unsaturation; aromatic heterocycles having at least one hetero atom selected from N, O and S atoms; isomers of such heterocycles and combinations thereof. In addition, suitable heterocycles may include, for example, 5 to 7-membered heterocycles that are fused together to form larger 9 to 14 membered heterocycles having at least one N, O or S atom; isomers of such heterocycles and combinations thereof. Additional heterocycles suitable for use with the present invention include 5 to 7-membered heterocycles that are fused with a carbocycle to form larger 9 to 14-membered heterocycles.

In another embodiment, the antibacterial polymer emulsion of the present invention include the copolymer B comprising a heterocyclic group selected from imidazole; thiophene; pyrrole; oxazole; thiazoles and their respective isomers (e.g., thiazol-4-yl, thiazol-3-yl and thiazol-2-yl); tetrazole; pyridine; pyridazine; pyrimidine; pyrazine; azoles; indazoles; triazoles and their respective isomers (e.g., 1,2,3-triazole and 1,2,4-triazole); and combinations thereof, such as imidazole 1,2,3-triazole-1,2,4-triazole ; benzotriazole; methyl-benzotriazole; benzothiazole; methylbenzothiazole; benzimidazole and methyl benzimidazole. In one aspect of this embodiment, the antibacterial polymer emulsion of the present invention includes a copolymer comprising a heterocycle group selected from imidazole, benzotriazole and benzimidazole.

In another embodiment of the present invention, the antibacterial polymer emulsion comprises a heterocyclic containing monomer and a non-heterocyclic containing monomer. In one aspect of this embodiment, the ratio of the heterocyclic containing monomer to the non-heterocyclic containing monomer is 95:5 to 5:95; alternatively 80:20 to 20:80; alternatively 60:40 to 40:60. In one aspect of this embodiment, the heterocyclic containing monomer is vinylimidazole.

In another embodiment of the present invention, the antibacterial polymer emulsion comprises a heterocyclic containing monomer complexed with silver. In one aspect of this embodiment, the weight ratio of the heterocyclic containing monomer to silver is 95:5 to 5:95; alternatively 90:10 to 10:90; alternatively 80:20 to 20:80. In another aspect of this embodiment, the molar ratio of the silver to the heterocyclic containing monomer is 10:1 to 1:10; alternatively 4:1 to 1:4; alternatively 2:1 to 1:2. In yet another aspect of this embodiment, the heterocyclic containing monomer is vinylimidazole.

In another embodiment of the present invention, the polymer B comprises 0.5 to 60 wt % cross-linker, alternatively at least 2 wt % cross-linker, alternatively at least 5 wt % cross-linker, alternatively at least 8 wt % cross-linker, alternatively at least 10 wt % cross-linker.

Cross-linkers suitable for use with the present invention include any known cross-linking material provided that the physical and chemical stability of the antibacterial polymer emulsion is substantially unaffected by inclusion of the cross-linking material. Examples of cross-linkers suitable for use with the present invention included, but are by no means limited to, di-, tri-, tetra- and higher multi-functional ethylenically unsaturated monomers such as, trivinylbenzene; divinyltoluene; divinylpyridine; divinylnaphthalene; divinylxylene; ethyleneglycol diacrylate; trimethylolpropane triacrylate; diethyleneglycol divinyl ether; trivinylcyclohexane; allyl methacrylate ("ALMA"); ethyleneglycol dimethacrylate ("EGDMA"); diethyleneglycol dimethacrylate ("DEGDMA"); propyleneglycol dimethacrylate; propyleneglycol diacrylate; trimethylolpropane trimethacrylate ("TMPTMA"); divinylbenzene ("DVB"); 2,2-dimethylpropane-1,3-diacrylate; 1,3-butyleneglycol diacrylate; 1,3-butyleneglycol dimethacrylate; 1,4-butanediol diacrylate; diethyleneglycol diacrylate; diethyleneglycol dimethacrylate; 1,6-hexanediol diacrylate; 1,6-hexanediol dimethacrylate; tripropyleneglycol diacrylate; triethyleneglycol dimethacrylate; tetraethyleneglycol diacrylate; polyethyleneglycol 200 diacrylate; tetraethyleneglycol dimethacrylate; polyethyleneglycol dimethacrylate; ethoxylated bisphenol A diacrylate; ethoxylated bisphenol A dimethacrylate; polyethyleneglycol 600 dimethacrylate; poly(butanediol)diacrylate; pentaerythritol triacrylate; trimethylolpropane triethoxy triacrylate; glycerylpropoxy triacrylate; pentaerythritol tetraacrylate; pentaerythritol tetramethacrylate; dipentaerythritol monohydroxypentaacrylate; divinyl silane; trivinyl silane; dimethyl divinyl silane; divinyl methyl silane; methyl trivinyl silane; diphenyl divinyl silane; divinyl phenyl silane; trivinyl phenyl silane; divinyl methyl phenyl silane; tetravinyl silane; dimethyl vinyl disiloxane; poly(methyl vinyl siloxane); poly(vinyl hydrosiloxane); poly(phenyl vinyl siloxane) and mixtures thereof.

In another embodiment of the present invention, the Tg of the copolymer B is from −35° C. to 60° C., preferably from −15° C. to 40° C., and more preferably from −10° C. to 30° C.

In another embodiment of the present invention, the copolymer B exhibits an average particle size of less than 200 nm; alternatively less than 50 nm; alternatively of 1 to 10 nm; alternatively less than 10 nm; alternatively of 1 to 8 nm; alternatively of less than 5 nm.

In another embodiment of the present invention, the copolymer B exhibits a molecular weight of less than 500,000; alternatively of less than 100,000; alternatively of less than 50,000; alternatively of 500 to 5,000.

The aqueous antibacterial polymer emulsion of the present invention comprises, by weight percentage based on the dry weight of the emulsion, from 0.004 to 10%, alternatively from 0.05 to 2%, alternatively from 0.1 to 2%, alternatively from 0.2 to 2%, an oxidant compound as additive. Examples of suitable oxidant include peroxides such as, for example, peroxide hydrogen, benzoyl peroxide, tert-butyl hydro peroxide, di-tert-butyl hydro peroxide, tert-butyl peroxy benzoate and tert-butyl peroxy-2-ethyl-hexanoate; halic acids such as, for example, chloric acid, bromic acid and iodic acid; hypohalous acid such as, for example, hypochlorous acid, hypobromous acid and hypoiodus acid; halous acid such as, for example, chlorous acid; perhalic acids such as, for example, perchloric acid, perbromic and periodic acid; and their lithium, sodium and calcium salts such as, for example, lithium perchlorate, potassium chlorate, sodium chlorite, potassium bromate, sodium iodate, sodium hypochlorite, calcium chlorate and calcium iodate; and the combinations thereof.

In another embodiment of the present invention, the antibacterial polymer emulsion could be insufflated with vapor, air, nitrogen or other gas, wherein the gas prefer vapor. After the stripping, the VOC and/or the ammonia in the antibacterial polymer emulsion could be taken out by the vapor, air, nitrogen or other gas. An example of the stripped antibacterial polymer emulsion is with 0 to 800 ppm VOC and no ammonia odor.

The antibacterial emulsion of the present invention is heat stable. The term "heat stable" of a polymer emulsion or a coating composition as used herein and in the appended claims refers to a durability characteristic of the polymer emulsion or the coating composition upon heating at a temperature of at least 40° C., alternatively at least 50° C., alternatively at least 80° C., alternatively at least 100° C. for a period of at least 10 days. The heat durability of the emulsion or the composition can be visual scored as from level 5 to level 0 which stands for from no visible change to heavy discoloration, as detailed described in the Example part; or measured by the Hunter Color test methods (Billmeyer, Jr. et al., PRINCIPLES OF COLOR TECHNOLOGY, John Wiley & Sons, $2^{ED}$ (1981)). In the present invention, the discoloration upon such heating is acceptable when the visual scored level reaches level 3 or higher, alternatively reaches level 4 or higher. By "acceptable" herein is meant sufficient coloration stability suitable for the application in the antimicrobial compositions of the present invention. An embodiment with "acceptable" discoloration properties is regarded as within the scope of the present invention.

The term "antibacterial polymer emulsion" as used herein and in the appended claims refers to an emulsion exhibits one or more of the following properties—the inhibition of the growth and the killing of bacteria or other microbes in the emulsion, and inhibition of the growth and the killing of bacteria or other microbes on surface of an article coated by the coating composition or in a radius extending from the article (hereinafter collectively referred to as "microbial production").

The present invention further provides an aqueous coating composition comprising: the aqueous antibacterial polymer emulsion of the present invention and a pigment, wherein the pigment is a rutile type titanium dioxide; and wherein the coating composition is light and heat stable. Preferably, the pigment is silica or alumina modified rutile type titanium dioxide. More preferably, the pigment is silica modified rutile type titanium dioxide.

The amount of the pigment in the coating composition ranges from 10 wt % to 60 wt %, preferably from 15 to 50 wt %, more preferably from 22 to 50 wt %, based on the dry weight of the composition.

The antibacterial coating composition of the present invention inhibit the microbial production by at least 25%; alternatively, the antibacterial coating composition of the present invention exhibit at least a 1-log reduction (≥90% inhibition) of microbial colony forming units per mL; alternatively the antibacterial coating composition of the present invention exhibit at least a 2-log reduction (≥99% inhibition) of microbial colony forming units per mL; alternatively the antibacterial coating composition of the present invention exhibit at least a 6-log reduction (≥99.9% inhibition) of microbial colony forming units per mL. Such microbes include, but are not limited to, *Aureobasidium pullulans, Bacillus cereus, Bacillus thuringiensis, Chaetomium globosum, Enterobacter aerogines, Escherichia coli, Gliocladtum virens, Klebsiella Pheumoniae, Legionella pneumpophila, Listeria Monocytogenes, Mycobacterium tuberculosis, Porphyromonas gingivalis, Proteus mirabilis, Proteus vulgaris, Pseudomonas aeruginosa, Saccharomyces cerevisiae, Salmonella gallinarum, Salmonella typhimurium, Staphylococcus aureus, Staphylococcus epidermidis, Streptococcus agalactiae, Streptococcus faecalis, Streptococcus mutans, Trycophyton malmsten, Vibrio parahaemolyticus, Stachybotrys, Aspergillus niger, Candida albicans* and *Penicillium funiculosum*.

The antibacterial coating composition of the present invention is heat and light stable. The term "light stable" of a coating composition as used herein and in the appended claims refers to a durability characteristic of the coating composition upon exposure to light in the visible and/or ultraviolet spectrum. The light durability of the emulsion or the composition can be visual scored or measured by the Hunter Color test methods aforementioned. In the present invention, the discoloration upon 45 days' interior exposure at the window side is acceptable when the individual values of Hunter L, a, b and L*a*b* (CIELAB) exhibits a delta b of less than 1.4; the discoloration upon 500 hours' 317 nm QUV exposure is acceptable when delta b is less than 2.45; and the discoloration upon 7 days' exterior exposure is acceptable when delta b is less than 3.5.

The aqueous coating composition can be used for coating of an article which possesses an antibacterial surface, wherein the coating method comprising steps of:

(1) forming an aqueous coating composition described in the second aspect of the invention;

(2) applying said aqueous coating composition to a surface of an article; and (3) drying, or allowing to dry, said aqueous coating composition.

The aqueous coating composition of this invention is contemplated to encompass coating or paint compositions which may be described in the art as high gloss, gloss, semi-gloss, low gloss or flat coatings, primers, textured coatings, and the like. The aqueous coating composition is prepared by techniques which are well known in the coatings art. First, optionally, at least one pigment is well dispersed in an aqueous medium under high shear such as is afforded by a COWLES mixer or, in an alternative, at least one predispersed pigment may be used. Then the aqueous emulsion copolymer is added under low shear stirring along with other coatings adjuvants, as desired. Alternatively, the aqueous emulsion copolymer may be included in the optional pigment dispersion step. The aqueous composition may contain conventional coatings adjuvants such as, for example, tackifiers, emulsifiers, coalescing agents such as for example, TEXANOL™ (Eastman Chemical Co.), cosolvents such as, for example, glycols and glycol ethers, buffers, neutralizers, thickeners or rheology modifiers, humectants, wetting agents, biocides, plasticizers, antifoaming agents, colorants, waxes, and anti-oxidants.

The solids content of the aqueous coating composition may be from about 10% to about 70% by volume. The viscosity of the aqueous coating composition may be from 0.05 to 30 Pa·s (50 cps to 30,000 cps), as measured using a Brookfield viscometer; the viscosities appropriate for different application methods vary considerably.

The aqueous coating composition may be applied by conventional application methods such as, for example, brushing, roller application, and spraying methods such as, for example, air-atomized spray, air-assisted spray, airless spray, high volume low pressure spray, and air-assisted airless spray.

The antibacterial polymer emulsion of the present invention may be used in a variety of materials to provide a persistent, antibacterial activity with low discoloration level upon exposure to light and/or heat The materials include, for example, plastics, emulsions, dispersions, paints, latices, coatings, construction products (such as mastics, caulks and sealants), construction adhesives (such as ceramic adhesives, carpet backing adhesives, and laminating adhesives), industrial or consumer adhesives, photographic chemicals, printing fluids, household products (such as bathroom disinfectants or sanitizers), cosmetics and toiletries, shampoos, soaps, detergents, industrial disinfectants or sanitizers (such as cold sterilants and hard surface disinfectants), floor polishes, laundry rinse water, metalworking fluids, conveyor lubricants, hydraulic fluids, leather and leather products, textiles, textile products, wood and wood products (such as plywood, chipboard, flakeboard, laminated beams, oriented strandboard, hardboard and particleboard), petroleum processing fluids, fuel, oilfield fluids (such as injection water, fracture fluids and drilling muds), agricultural adjuvant preservation, surfactant preservation, diagnostic reagent preservation and filtration media.

In another embodiment, the antibacterial polymer emulsion of the present invention may be added into an environment for remediation purposes. For example, the antibacterial polymer emulsion of the present invention may be added to bio-contaminated formulations for the remediation of such contaminated formulations.

The antibacterial coating composition of the present invention may be used in a variety of materials to provide antibacterial surfaces exhibiting persistent, antibacterial activity with low discoloration level upon exposure to light and/or heat. The materials subjected to the coating composition include, for example, plastic, wood, metal, primed surfaces, previously painted surfaces, and cementitious substrates.

In the present specification, the technical features in each preferred technical solution and more preferred technical solution can be combined with each other to form new technical solutions unless indicated otherwise. For briefness, the Applicant omits the descriptions for these combinations. However, all the technical solutions obtained by combing these technical features should be deemed as being literally described in the present specification in an explicit manner.

EXAMPLES

The experimental methods in the examples, when not described in detail, is contemplated to follow normal conditions in the art, for example, handbooks of polymer chemistry, or follow conditions suggested by chemical or instrument manufacturer.

I. Raw Materials

| A) Starting materials used in making Latex compound | |
|---|---|
| Compound | Chemical Nature |
| BA | Butyl Acrylate |
| VA | Vinyl acetate |
| ST | Styrene |
| MMA | Methyl Methacrylate |

-continued

| | |
|---|---|
| (M)AA | (Meth)acrylic Acid |
| SSS | Sodium styrene sulfonate |
| AMPS | Sodium-2-acrylamido-2-methylpropane sulfonic acid |
| SilvaDur ™ | Silver ion complex with polyimidazole |
| $H_2O_2$ | Hydrogen peroxide |
| BPO | Benzoyl peroxide |
| $KBrO_3$ | Potassium bromate |
| APS | Ammonium persulfate |
| EDTA | Ethylenediaminetetraacetic acid |
| SBS | Sodium bisulfite |
| DBS | sodium dodecyl benzene sulfonate |
| FA-40 | fatty alcohol ethoxylate EO: 40 |
| MIT | 2-Methyl-4-isothiazolin-3-one |
| NXZ ™ | Defoamer |

B) Starting materials used in paint formulation

| Material | Function | Chemical nature | Supplier |
|---|---|---|---|
| Primal ™ RM-8W | Thickener | HEUR | Rohm and Haas |
| Acrysol ™ AP-10 | Thickener | Hydrophobically modified alkali soluble emulsion | Rohm and Haas |
| Natrosol ™ 250 HBR | Thickener | Hydrophobic modified cellulose | Aqualon |
| Propylene Glycol | Solvent | Propylene glycol | |
| Ethylene Glycol | Solvent | Ethylene glycol | |
| AMP-95 ™ | Base | 2-methyl-2-amino-propanol | Dow |
| Oratan ™ 731A | Pigment dispersant | Polyacid Copolymer | Rohm and Haas |
| Orotan ™ 1288 | Pigment dispersant | Polyacid | Rohm and Haas |
| Triton ™ CF-10 | Wetting agent | Nonionic surfactant | Union Carbide |
| Dispalair ™ CF-246 | Defoamer | | Blackburn Chemicals |
| Ti-Pure ™ R-706 | Pigment | Titanium dioxide | DuPont |
| Ti-Pure ™ R-902 | Pigment | Titanium dioxide | DuPont |
| TRONOX ™ CR-828 | Pigment | Titanium dioxide | Kerr-McGee Corp |
| BA-01 | Pigment | Titanium dioxide | |
| CC-700 | Extender | Calcium carbonate | Guangfu Building Materials Group (China) |
| CC-1000 | Extender | Calcium carbonate | Guangfu Building Materials Group (China) |
| ASP-170 ™ | Extender | Delaminated clay | Engelhard |
| DB-80 | Extender | Calcined clay | Jinyang Gaoling Lt. Co. (China) |
| $H_2O_2$ | oxidant | Hydrogen Peroxide | |
| Texanol ™ | Coalescent | Trimethylpentanediol isobutyrate | Eastman |
| Ropaque ™ Ultra E | Opaque polymer | polystyrene | Rohm and Haas |

II. Test Procedures

Antibacterial Efficacy of the Dry Coating Film

The antibacterial efficacy test of the dry film follows the Chinese standard GB/T 21866-2008, which is modified from JIS Z 2801. The detail information of the test method is described as following:

Inoculum preparation: transferred test *Escherichia coli* organisms onto tryptic soy agar (TSA) slant and incubated at 37° C. for 18~20 hours, transferred the organisms to another fresh TSA slant and incubated again. Diluted the cultured colony in 1/500 tryptic soy broth (TSB) solution (TSB diluted by 0.85% NaCl solution), and diluted *Staphylococcus aureus* colony in 1/100 TSB solution, to achieve $5.0~10.0\times10^5$ cfu/mL, respectively.

Test specimen preparation: coated a plastic test panel with the antibacterial coating composition, dried and cut the panel with dry film into 50 mm×50 mm squares.

Blank control: dry-film panel coated with a coating composition without the metal complexed with a copolymer or the oxidant.

Test procedure: placed the test specimen in sterilized petri dish. Added 0.4~0.5 mL inoculum onto blank control and test specimen respectively, covered the inoculum with sterile plastic film and avoided bubble. Incubated the dishes at 37° C. and under relative humidity (RH)>90% for 24 hours. Rinsed the specimen with 20 mL elution solution (0.85% NaCl solution, pH 7.0~7.2), added 1 mL the elution solution containing residue microbes onto a nutrition agar dish, incubated at 37° C. for 24 hours and enumerated the microbe colony by the method in Chinese Standard GB/T 4789.2. Made 2 duplicates for each sample.

Calculation of the antibacterial efficiency according to:

$$\text{Antibacterial efficacy } R\ (\%)=(B-C)/B\times100$$

wherein B(cfu) refers to average residue microbe content of the blank control after 24 h incubation and C(cfu) refers to average residue microbe content of the test specimen after 24 hours incubation.

Light Stability Test of the Dry Coating of the Antimicrobial Coating Composition The light stability of the antibacterial coating composition was tested by measuring the individual values of Hunter L, a, b and L*, a*, b* (CIELAB) before and after exposure of the dry coating film to the sun light or UV for at least 1 week. Prepared the coating film according to Chinese Standard GB/T 1727 and dried at 25° C. and 50% relative humidity (RH) for at least 7 days. The dry film were exposed outdoor and near window in house (where sunlight can directly reach through glass) and UV for at least 1 week.

Heat Stability Test of the Antimicrobial Polymer Emulsion or Coating Composition The heat stability was evaluated by heating the emulsion or composition in an oven for at least 10 days. Added 100 mL the emulsion or composition into a 200 mL heat stable plastic container and placed into the oven of 50° C. for at least 10 days. By comparing the appearance between the heated and unheated sample, the statuses of the samples were visual scored as from level 5 to level 0 which correspond to values of Hunter L, a, b and L*, a*, b* (CIELAB) as:

5—no visible change, correspond to delta b/b* value of less than 2;

4—slight yellowing, correspond with delta b/b* value of 2~3;

3—obvious yellowing, correspond with delta b/b* of value 3~4;

2—slight blue or dark, correspond with delta b/b* value of 4~5;

1—obvious blue or dark, correspond with delta L/L* plus delta b/b* value of 5~10; and 0—heavy discoloration, correspond with delta L/L* plus delta b/b* value of higher than 10.

Example 1

Preparation of Aqueous Emulsion Polymers

Latex 1

A monomer emulsion was prepared by combining 961.0 g BA, 633.3 g MMA, 32.9 g MAA, 430.0 g DI Water, and 36.0 g of a 22.5 wt % aqueous solution of DBS, and emulsifying with stirring. Next, 11.5 g of a 22.5 wt % aqueous solution of DBS and 820.0 g DI water were charged to a five liter multi-neck flask fitted with mechanical stirring. The contents of the flask were heated to 85° C. under a nitrogen atmosphere and stirred. To the stirred flask, 5.7 g $Na_2CO_3$ in 35.0 g DI water, 89.0 g of the monomer emulsion were added, followed by 3.3 g APS in 26 g DI water. The remaining monomer emulsion and a solution of 1.5 g APS in 88.5 g DI water were then added to the flask over 120 minutes. Reactor temperature was maintained at 85° C. Next, 30 g DI water was used to rinse the emulsion feed line to the reactor. After cooling the contents of the reactor to 75° C., 0.01 g ferrous sulfate and 0.01 g EDTA, 1.4 g of t-butyl hydroperoxide (70% aq.), and 1.1 g of isoascorbic acid in aqueous solutions were added to the flask. The contents of the flask were neutralized to a pH of 7.5 to 8.5 with sodium hydroxide or other non-volatile bases for low odor. To the cooled batch, 2.9 g hydrogen peroxide (30% aq.) in 6.2 g DI water was added to the flask. Then 11.2 g SilvaDur™ (3% $Ag^+$) was added to the flask followed by 0.7 g NXZ™ (Cognis). The calculated Tg of the copolymer was 9° C.

Latex 2 and Latex 3

The same process as for Latex 1 with, nevertheless, variations in amounts and in nature of monomers based on Table 1 was used to make Latex 2 and Latex 3.

Latex 4 to Latex 6

The same process as for Latex 1, 2, 3, nevertheless, without neither silver nor oxidant based on Table 1 was used to make Latex 4 to Latex 6.

Latex 7 to Latex 17

The same process as for Latex 1 with, nevertheless, variations in amounts and in nature of silver or oxidant based on Table 1 was used to make Latex 7 to Latex 17.

Latex 18

The same process as for Latex 1 with nevertheless, variations in type of silver ion based on Table 1 was used to make Latex 18.

Latex 4 to Latex 7 and Latex 18 were out of the invention.

TABLE 1

Formulation and heat stability of polymer emulsion

| Latex | Polymer A composition (%, w/w) | Oxidant ($H_2O_2$, ppm, w/w) | Metal (SilvaDur™, Ag ppm, w/w) | heat stability[#] |
|---|---|---|---|---|
| 1 | 38.92 MMA/59.06 BA/ 2.02 MAA | 500 | 200 | 5 |
| 2 | 38.92 ST/59.06 BA/ 2.02 AA | 500 | 200 | 5 |
| 3 | 68.26 VA/31.24 BA/ 0.50 AA | 1000 | 200 | 5 |
| 4 | 38.92 MMA/59.06 BA/ 2.02 MAA/ | 0 | 0 | 5 |
| 5 | 38.92 ST/59.06 BA/ 2.02 AA | 0 | 0 | 5 |
| 6 | 68.26 VA/31.24 BA/ 0.50 AA | 0 | 0 | 5 |
| 7 | 38.92 MMA/59.06 BA/ 2.02 MAA | 0 | 200 | 2 |
| 8 | 38.92 MMA/59.06 BA/ 2.02 MAA | 40 | 200 | 3 |
| 9 | 38.92 MMA/59.06 BA/ 2.02 MAA | 2,000 | 200 | 5 |
| 10 | 38.92 MMA/59.06 BA/ 2.02 MAA | 20,000 | 200 | 5 |
| 11 | 38.92 MMA/59.06 BA/ 2.02 MAA | 250 | 20 | 5 |
| 12 | 38.92 MMA/59.06 BA/ 2.02 MAA | 2500 | 5,000 | 5 |
| 13 | 38.92 MMA/59.06 BA/ 2.02 MAA | 5000 | 10,000 | 4 |
| 14 | 68.26 VA/31.24 BA/ 0.50 AA | 1,000 | 267 | 4 |
| 15 | 68.26 VA/31.24 BA/ 0.50 AA | 2,000 | 267 | 5 |
| 16 | 68.26 VA/31.24 BA/ 0.50 AA | 2,000* | 267 | 5 |
| 17 | 68.26 VA/31.24 BA/ 0.50 AA | 2,000** | 267 | 5 |
| 18 | 68.26 VA/31.24 BA/ 0.50 AA | 1,000 | 200*** | 2 |

*BPO instead of $H_2O_2$
**$KBrO_3$ instead of $H_2O_2$
***$AgNO_3$ instead of SilvaDur™ and was calculated by silver ion concentration
[#]the latex was heated under 50° C. for 10 days and the color status of the latex in can was leveled as 0~5

Example 2

Preparation of Aqueous Coating Compositions

Paint 1

A paint containing Latex 1 of Example 1 was prepared using the following process. The ingredients listed in Table 2 (grind) were mixed using a high speed Cowles disperser. The ingredients listed in Table 2 (let down) were added using a conventional lab mixer. The pigment volume concentration (PVC) of the resulting paints was 55%. The volume solids of the resulting paint was 38.5%. And the weight solids was 52.2%.

TABLE 2

55.2% PVC Aqueous Coating Composition
Paint formulation

| Material | Weight (g) |
|---|---|
| Grind | |
| Water | 160.9 |
| Propylene glycol | 15.0 |
| Acrysol™ AP-10 | 1.0 |
| AMP-95™ | 0.5 |
| Orotan™ 731A | 11.0 |
| Triton™ CF-10 | 1.5 |
| Dispelair™ CF-246 | 1.0 |
| Ti-Pure™ R-706 | 175.0 |
| CC-1000 | 170.5 |
| Letdown | |
| Latex 1 | 322.0 |
| Ropaque Ultra E | 100.0 |
| Dispelair™ CF-246 | 1.0 |
| Texanol™ | 5.3 |
| Primal™ RM-8W | 3.3 |
| Water | 32.0 |
| Total | 1000.0 |

Paint 2 to Paint 17

Paint 2 to Paint 17 (containing Latex 2 to Latex 17 respectively) were prepared following the process of Paint 1. Appropriate adjustment of water and binder weights were done such that the resulting paints had a PVC of 55.2%, a volume solid of 38.5% and a weight solids of 52.2%.

Paint 4 to Paint 6 and Paint 7 were out of the invention.

Paint 18 to Paint 23

Paint 18 to Paint 23 containing Latex 1 of Example 1 were prepared using the same process of Paint 1 with, nevertheless, variations in amounts and in nature of Titanium Dioxide based on Table 3. The PVC of the resulting paints was 55.2%. The volume solids of the resulting paint was 38.5%. Paint 23 was out of the invention.

TABLE 3

TiO$_2$ type and amount of Paint 18 to Paint 23

| Paint ID | Latex ID | TiO$_2$ Name | Type | PVC (%) | Amount (wt %, dry) |
|---|---|---|---|---|---|
| 18 | 1 | R-706 | Rutile | 5 | 11.2 |
| 19 | | R-706 | Rutile | 10 | 22.5 |
| 20 | | R-706 | Rutile | 25 | 51.0 |
| 21 | | R-902 | Rutile | 15 | 33.5 |
| 22 | | CR-828 | Rutile | 15 | 33.5 |
| 23 | | BA-01 | Anatase | 15 | 33.5 |

Paint 24 and Paint 25

Paint 24 and Paint 25 containing aqueous emulsion polymer Latex 1 were prepared using the same process of Paint 1 with, nevertheless, variations in total PVC. The ingredients of Paint 24 were similar with in Table 2 except the level of Latex 1. The ingredients of Paint 25 were listed in Table 4. Let down were added using a conventional lab mixer. The resulting Paint 25 had a PVC of 78.6%, a volume solids of 32.4% and a weight solids of 53.5%.

TABLE 4

78.6% PVC Aqueous Coating Composition Paint formulation

| Material | Weight (g) |
|---|---|
| Grind | |
| Water | 367.8 |
| Ethylene glycol | 7.4 |
| Natrosol 250 HBR | 5.9 |
| AMP-95 ™ | 0.5 |
| Orotan ™ 1288 | 3.9 |
| Triton ™ CF-10 | 1.0 |
| Dispelair ™ CF-246 | 1.0 |
| Ti-Pure ™ R-706 | 54.0 |
| CC-700 | 157 |
| CC-1000 | 113 |
| ASP-170 ™ | 98 |
| DB-80 | 59 |
| Letdown | |
| Latex 1 | 120 |
| Dispelair ™ CF-246 | 0.3 |
| Texanol ™ | 1.6 |
| Water | 9.6 |
| Total | 1000.0 |

III. Properties of Aqueous Coating Compositions

Table 5 listed the antibacterial property of the dry film of Paint 1 to Paint 3 (Paint 4 to paint 6 were used as blank control), Paint 11 to Paint 13 (paint 4 as blank control) and Paint 18 to Paint 25 (paint 4 as blank control).

TABLE 5

Antibacterial property of dry paint film

| Paint ID | Staphylococcus aureus** cfu/test specimen 1 | 2 | Antibacterial ratio (R %)* | Escherichia coli** cfu/test specimen 1 | 2 | Antibacterial ratio (R %)* |
|---|---|---|---|---|---|---|
| 4 | 992,000 | 768,000 | Control | 288,000 | 57,600 | Control |
| 1 | <20 | <20 | >99.9 | <20 | <20 | >99.9 |
| 5 | 912,000 | 960,000 | Control | 944,000 | 992,000 | Control |
| 2 | <20 | <20 | >99.9 | <20 | <20 | >99.9 |
| 6 | 2,720,000 | 2,400,000 | Control | 52,000 | 56,000 | Control |
| 3 | <20 | <20 | >99.9 | <20 | <20 | >99.9 |

**The inoculum of S. aureus was 1,400,000 cfu/test specimen. The inoculum of E. coli was 1,800,000 cfu/test specimen.

| Paint ID | 1 | 2 | R % | 1 | 2 | R % |
|---|---|---|---|---|---|---|
| 4 | 55,000 | 68,000 | Control | 358,000 | 304,000 | Control |
| 11 | 59,000 | 11,000 | 41.9% | 59,000 | 170,000 | 63.8% |
| 12 | <20 | <20 | >99.9 | <20 | <20 | >99.9 |
| 13 | <20 | <20 | >99.9 | <20 | <20 | >99.9 |

**The inoculum of S. aureus was 2,000,000 cfu/test specimen. The inoculum of E. coli was 7,000,000 cfu/test specimen.

| Paint ID | 1 | 2 | R % | 1 | 2 | R % |
|---|---|---|---|---|---|---|
| 4 | 912,000 | 960,000 | Control | 944,000 | 992,000 | Control |
| 18 | <20 | <20 | >99.9 | <20 | <20 | >99.9 |
| 19 | <20 | <20 | >99.9 | <20 | <20 | >99.9 |
| 20 | <20 | <20 | >99.9 | <20 | <20 | >99.9 |
| 21 | <20 | <20 | >99.9 | <20 | <20 | >99.9 |
| 22 | <20 | <20 | >99.9 | <20 | <20 | >99.9 |
| 23 | <20 | <20 | >99.9 | <20 | <20 | >99.9 |
| 24 | <20 | <20 | >99.9 | <20 | <20 | >99.9 |
| 25 | <20 | <20 | >99.9 | <20 | <20 | >99.9 |

**The inoculum of S. aureus was 12,000,000 cfu/test specimen. The inoculum of E. coli was 47,000,000 cfu/test specimen.

*The antibacterial ratio of each test specimen was a relative ratio based on its corresponding blank control.

Table 6 listed the coloration stability properties of the dry paint film of the antibacterial coating compositions under light and the wet latex paints under heat environment.

TABLE 6

Coloration stability properties of dry paint film

| Paint ID | latex ID | 45 days exposure at the window side* | 500 hours QUV** | 7 days exposure out side*** | Wet paint heat stability 10 days heat age, evaluated by in-can status (0~5) |
|---|---|---|---|---|---|
| 1 | 1 | 0.71 | 1.77 | 2.11 | 5 |
| 2 | 2 | 0.30 | 1.75 | 1.02 | 5 |
| 3 | 3 | 0.71 | 1.54 | 1.48 | 5 |
| 4 | 4 | 0.32 | 1.09 | 1.01 | 5 |
| 5 | 5 | 0.28 | 2.04 | 0.96 | 5 |
| 6 | 6 | 0.01 | 1.34 | 0.70 | 5 |
| 7 | 7 | 1.53 | 2.95 | N/A | 4 |
| 8 | 8 | 1.12 | 2.23 | N/A | 5 |
| 9 | 9 | 0.78 | 1.65 | 2.01 | 5 |
| 10 | 10 | 0.56 | 1.45 | N/A | 5 |
| 11 | 11 | 0.35 | 1.49 | 1.23 | 5 |
| 12 | 12 | N/A | 2.19 | N/A | 5 |
| 13 | 13 | N/A | 2.32 | N/A | 4 |
| 14 | 14 | 0.89 | 1.89 | 1.56 | 5 |
| 15 | 15 | 0.92 | 1.82 | 1.61 | 5 |
| 16 | 16 | 1.21 | N/A | N/A | 5 |
| 17 | 17 | 0.58 | N/A | N/A | 5 |
| 18 | 1 | 1.36 | 2.43 | 3.51 | 5 |
| 19 | | 1.03 | 1.95 | 2.65 | 5 |
| 20 | | 0.85 | 1.76 | N/A | 5 |
| 21 | | 0.66 | 1.83 | 1.83 | 5 |

TABLE 6-continued

Coloration stability properties of dry paint film

| Paint ID | latex ID | values of delta b (Hunter L, a, b) | | | Wet paint heat stability |
| --- | --- | --- | --- | --- | --- |
| | | 45 days exposure at the window side* | 500 hours QUV** | 7 days exposure out side*** | 10 days heat age, evaluated by in-can status (0~5) |
| 22 | | 1.00 | 1.79 | 2.85 | 5 |
| 23 | | 4.22 | N/A | 4.40 | 5 |

*It was an indoor exposure test conducted at side of a window where sunlight could reach the film well. It was to simulate the interior wall paint environment. The coloration stability would be acceptable when delta b was less than 1.4.
**The QUV was QUV-B with wavelength of 317 nm. The coloration stability would be acceptable when delta b was less than 2.45.
***The direction of outdoor exposure was south, 45 degree slope at an exposure site of Shanghai, China. The coloration stability would be acceptable when delta b was less than 3.5.
N/A means did not test at that point.

The results in the above table indicated that the UV light would cause heavy discoloration of the films which contained the silver ion. The oxidants helped to improve color stability of the polymer emulsions and prevent discoloration in the dry coating films. The trend of the wet paints under heat environment was similar. The $TiO_2$ in the coating compositions played an important role in preventing the films from discoloring. The Rutile type $TiO_2$ was more effective than the anatase type $TiO_2$ in keeping coloration stability of the films.

The invention claimed is:

1. An aqueous antibacterial polymer emulsion comprising, based on the dry weight of the emulsion, from 90 to 99.9 wt % of a polymer A comprising acrylic, styrene-acrylic, or vinyl acetate-acrylic emulsion polymers, from 0.025 to 2 wt % of an oxidant selected from peroxides, halic acids, hypohalous acids, halous acids, perhalic acids, their salts, and combinations thereof, and from 0.002 to 0.5 wt % of silver, wherein the silver is complexed with a copolymer B that comprises from 5 to 95 wt % a heterocyclic containing monomer residue; and wherein the emulsion exhibits a delta b or delta b* of less than 2 after 10 days of heat aging at 50 °C.

2. The antibacterial polymer emulsion of claim 1, wherein the heterocyclic containing monomer residue is 1-vinylimidazole.

3. The antibacterial polymer emulsion of claim 1, wherein the emulsion comprises at least 50 ppm silver.

4. The antibacterial polymer emulsion of claim 1, wherein the emulsion is free of ammonia.

5. The antibacterial polymer emulsion of claim 1, wherein the emulsion has a volatile organic compounds content of 0 to 800 ppm.

6. An aqueous antibacterial coating composition comprising the polymer emulsion of claim 1 and from 10 to 60 wt %, based on the dry weight of the composition, a pigment, wherein the pigment is a rutile type titanium dioxide; wherein the coating composition exhibits a delta b or delta b* of less than 2 after 10 days of heat aging at 50 ☐C; and wherein a dried paint film derived from the coating composition exhibits a delta b or delta b* of less than 2.45 after 500 hours of QUV-B exposure.

7. The antibacterial coating composition of claim 6, wherein the amount of the pigment is from 22 to 50 wt % based on the dry weight of the composition.

8. The antibacterial coating composition of claim 6, wherein the pigment is silica or alumina modified rutile type titanium dioxide.

9. The antibacterial coating composition of claim 6, wherein the oxidant is present in an amount of 0.05 to 2 wt %; and wherein the silver is present in an amount of 0.05 to 0.5 wt %.

10. The antibacterial coating composition of claim 1, wherein the oxidant comprises hydrogen peroxide, benzoyl peroxide, tert-butyl hydroperoxide, di-tert-butyl hydroperoxide, tert-butyl peroxy benzoate, tert-butyl peroxy-2-ethylhexanoate or combinations thereof.

11. The antibacterial polymer emulsion of claim 1, wherein the oxidant comprises hydrogen peroxide.

* * * * *